United States Patent [19]

Otto et al.

[11] 4,049,729

[45] Sept. 20, 1977

[54] CHLORINATION OF BUTADIENE

[75] Inventors: Kenneth Wayne Otto, Victoria; Jimmy L. Hatten, Odessa, both of Tex.

[73] Assignee: E. I. Du Pont de Nemours and Company, Wilmington, Del.

[21] Appl. No.: 858,658

[22] Filed: Sept. 17, 1969

[51] Int. Cl.$^2$ .............................................. C07C 21/00
[52] U.S. Cl. .............................................. 260/654 H
[58] Field of Search ...................... 260/654 H, 662 R; 203/99; 202/153

[56] References Cited

U.S. PATENT DOCUMENTS

| 2,839,589 | 6/1958 | Brown | 260/654 |
|---|---|---|---|
| 2,928,884 | 3/1960 | Bellringer et al. | 260/654 |
| 3,472,902 | 10/1969 | Van Dijk | 260/654 |

*Primary Examiner*—Bernard Helfin
*Assistant Examiner*—A. Siegel

[57] ABSTRACT

A process of chlorinating butadiene in the vapor phase using a molar ratio of butadiene to chlorine of from 5:1 to 50:1 and preferably from 8:1 to 30:1 at from 70° to 250° C., separating the thus formed dichlorobutenes from the unreacted butadiene by condensing them in a scrubber-cooler wherein the heat required to vaporize the makeup liquid butadiene feed stream is provided by the condensing dichlorobutenes.

4 Claims, 1 Drawing Figure

U.S. Patent  Sept. 20, 1977  4,049,729
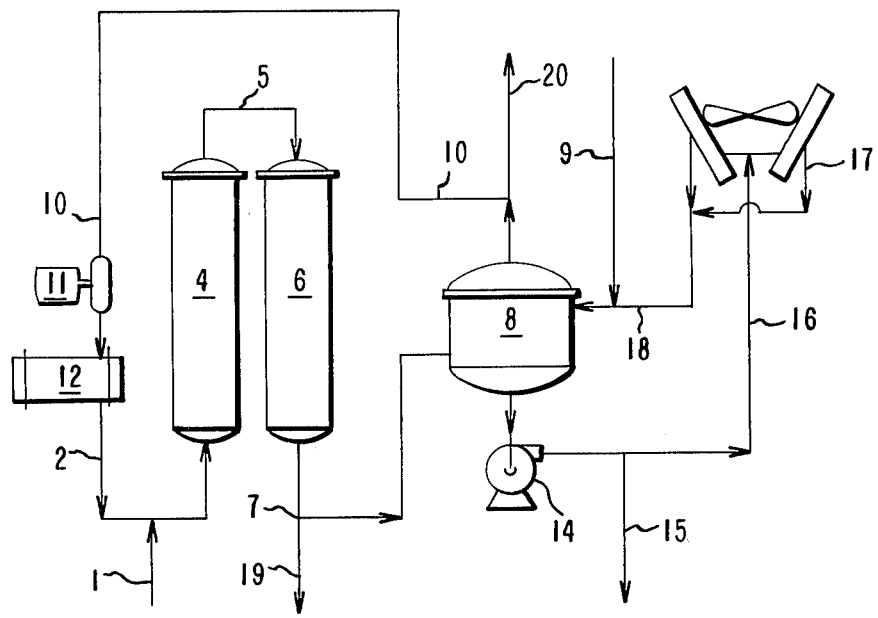
INVENTORS
KENNETH WAYNE OTTO
JAMES L. HATTEN
BY *William G. Hoffman*
AGENT

CHLORINATION OF BUTADIENE

SUMMARY OF THE INVENTION

This invention relates to an improved process for the production of dichlorobutenes from butadiene and chlorine.

This process involves the use of a substantially plug flow technique of reacting chlorine vapor and butadiene vapor (the latter at relatively low conversion) resulting in a high yield of dichlorobutenes.

More particularly, the process involves feeding a reactor with a mixture of butadiene vapor and chlorine vapor in a molar ratio of at least 5:1 up to 50:1 and preferably from 8:1 to 30:1 butadiene to chlorine. Preferably, substantially all of the chlorine is reacted before the reactants are removed from the reactor. The inlet temperature of the feed vapor to the reaction zone is preferably maintained at 70° to 175° C. The maximum temperature of the vapor mixture should be maintained below 250° C. and preferably is maintained below 230° C. The walls of the reactor in the zone where the bulk of the chlorination reaction occurs should be maintained preferably near the temperature of the vapor mixture so as to produce a substantially adiabatic reaction system and to discourage accumulation of liquid products on the walls of the reactor. This control of wall temperature may involve either adding or removing heat from the system depending on the conditions employed wherein the heat so removed or added is about 25 per cent or less of the heat of reaction. Thus, the reactor should be designed so as to provide a relatively high ratio of volume to surface area. The use of the lower temperatures of the present process reduces the buildup of coke-like material on the reactor walls and surprisingly results in higher yields as based on butadiene converted.

Under the conditions used in the present invention substantially all of the chlorine reacts with the butadiene. The per cent of dichlorobutenes produced is preferably maintained above 92 per cent as based on reacted butadiene. If the temperature of the reactants or the walls is so low as to permit condensation or if the temperature goes above 230° C. and especially at temperatures above 250° C., the amount of undesired materials produced goes up.

The reactor is generally tubular so as to achieve a substantially plug flow of reactants in about the last half of the reaction zone. Turbulence in the flow of the reactants and products through the reactor should be minimized in order to enhance plug flow. Generally, it is preferred to have the reactor situated vertically since a minimum of space is thus required. The volume of the reactor generally will be greater than 5 cubic feet and may be as large as practical engineering considerations will permit. It will preferably have an effective length to diameter ratio from the beginning to the end of the reaction zone of from 3:1 to 100:1. The reactor may be fed at one or more points depending on the configuration employed. Similarly, the reaction products may be removed from one or more points. The material of construction of the entire system should preferably be a one which does not interfere with the reaction or promote the formation or retention of condensate. Preferred materials include glass, nickel and nickel alloys such as Monel.

The pressure preferably is maintained at from about atmospheric pressure to about 100 psig. Normally, the pressure at the outlet end of the reaction zone will be less than 5 psi. below the pressure at the inlet end to the reaction zone.

The process of the present invention includes the separation of dichlorobutenes from the unreacted butadiene vapor present in the reactor effluent stream coupled with the recycle of the butadiene vapor back to the reactor. Prior processes recover the dichlorobutene product by cooling the reactor effluent stream to condense the dichlorobutenes and a large portion of the butadiene. This stream is then fed to a stripping column to recover the butadiene which is then compressed and scrubbed to remove by-product HCl before being recycled to the reactor system.

It is impractical to operate the process of the present invention with the prior art product recovery and butadiene recycle systems, because the high ratio of butadiene to chlorine in the reaction zone (low conversion per pass) requires the condensation of a relatiely large quantity of butadiene. This is a difficult and expensive recovery procedure. It is the unique combination of the reaction system and a simple product recovery and butadiene recycle process which gives the present process the high yield, and high purity dichlorobutene product at an attractive operating cost.

DESCRIPTION OF THE DRAWING

The drawing is a flow diagram of the process of the present invention.

In carrying out the present invention, chlorine vapor, stream 1, is combined with butadiene vapor, stream 2, to form feed stream 3 which is fed to the bottom of primary reactor 4 through tube 5 into secondary reactor 6. As indicated above the temperature of feed stream 3 should be from 70° to 175°C. and the temperature of the reactants in reactors 4 and 6 should not exceed 250° C. Upon leaving the reactor, the mixture stream 7 consisting principally of dichlorobutenes and butadiene together with by-product trichlorobutenes and tetrachlorobutanes is fed below the bottom tray of scrubber-cooler 8. Stream 9 of liquid or substantially liquid butadiene can either be premixed with stream 18 or separately fed to one of the upper trays in scrubber-cooler 8. The butadiene in this feed stream comprises the makeup butadiene entering the system and is introduced as a liquid so as to help condense the dichlorobutenes from the reactor stream. The latent heat of the condensing dichlorobutenes in the upper part of the scrubber-cooler vaporizes this butadiene. This total butadiene stream (unreacted plus makeup) leaving the top of scrubber-cooler 8 is then fed through stream 10 by means of recycle blower 11 through butadiene preheater 12 back to original butadiene feed stream 2. The crude dichlorobutene product is removed from the bottom of scrubber-cooler 8 through stream 13 by means of pump 14 and, if desired, removed from the system as product through stream 15. Additional removal of heat in the scrubber-cooler is conveniently done by recycling part of product stream 13 through stream 16 to heat exchanger 17 and back to one or more of the upper trays of scrubber-cooler 8 through stream 18. The relative amount and temperature of dichlorobutenes cooled and recycled should be such that the head temperature of the scrubber-cooler is maintained at from 45° to 80° C. and preferably from 45° to 65° C. At temperatures above 80° C., there may be as much as 11.7 weight per cent of dichlorobutenes in the recycle stream 10 which subsequently results in excessive formation of trichlorobutenes and tetrachlorobutanes. At a head temperature of 65° C. there may be as much as 4.6 weight per cent dichlorobutenes in the butadiene recycle feed stream 10. A purge of inert and gaseous by-products from the reactor system may be taken through stream 19 or 20.

The dichlorobutenes produced in the present invention are useful as nylon intermediates. For instance, they may be cyanated to form dicyanobutenes which, in turn, may be hydrogenated to produce hexamethylene diamine which is useful in the production of polyhexamethylene adipamide.

DESCRIPTION OF THE PREFERRED EMBODIMENTS

EXAMPLES I-V

A reaction system consisting of a reactor and a scrubber-cooler is set up as shown in the drawing. The reactor consists of a primary and a secondary reactor, each of which is a vertically disposed steam traced and lagged nickel clad tube which reactors are connected top to top. The scrubber-cooler has five trays. A steady state continuous reaction system is maintained by feeding liquid butadiene to the top tray of the scrubber-cooler at the rate indicated in Table I. The product from the reactor is fed below the bottom tray of the scrubber-cooler and the dichlorobutenes and the more highly chlorinated C-4 compounds are recovered from the bottom of the scrubber-cooler. The makeup butadiene fed to the scrubber-cooler and the unconverted butadiene separated from the reactor effluent stream are fed to the bottom of the primary reactor along with the mole per unit of chlorine indicated in Table I. Part of the product stream (crude dichlorobutenes) leaving the bottom of the scrubber-cooler is recycled through the heat exchanger and back to the top tray of the scrubber-cooler to provide additional cooling of the reactor effluent stream in the scrubber-cooler. In Table I, DCB stands for dichlorobutenes and pph stands for parts per hour (by weight).

TABLE I

|  | I | II | III | IV | V |
|---|---|---|---|---|---|
| Butadiene/Chlorine Ratio (Mole Ratio) | 15.3 | 14.2 | 14.6 | 19.9 | 13.4 |
| Reactor Pressure (psig) | 39 | 38.5 | 39 | 39 | 39.5 |
| Reactor Product Temp. Inlet Scrubber-Cooler (° C.) | 216 | 221 | 219 | 216 | 221 |
| Liquid Butadiene Make-up | | (90 psig and Ambient Temperature) | | | |
| Liquid Butadiene Make-up Flow to Scrubber-Cooler (pph) | 18.6 | 19.3 | 18.4 | 18.2 | 18.7 |
| DCB Coolant Flow to Scrubber-Cooler (pph) | 370 | 400 | 385 | 325 | 600 |
| DCB Coolant Temp. (° C) | 13 | 29 | 34 | 24 | 45 |
| DCB Liquid Product from Scrubber-Cooler (pph) | 30 | — | — | — | 28 |
| DCB Liquid Temp. Exit Scrubber-Cooler (° C) | 115 | 118 | 123 | 126 | 124 |
| Butadiene Vapor Flow Exit Scrubber-Cooler (pph) | 193 | 185 | 190 | 193 | 174 |
| Butadiene Vapor Temp. Exit Scrubber-Cooler (° C.) | 62 | 65 | 69 | 72 | 74 |
| By-product Trichlorobutenes, wt. % in Crude Liquid DCB (less butadiene) Exit Scrubber-Cooler | 0.49 | 0.48 | 0.53 | 0.60 | 0.86 |
| By-product Tetrachlorobutanes, wt. % in Crude Liquid DCB (less butadiene) Exit Scrubber-Cooler | 1.46 | 1.65 | 1.90 | 2.07 | 2.40 |
| DCB Exit top of Scrubber-Cooler, wt. % calculated from vapor pressure | 3.73 | 4.61 | 6.03 | 7.31 | 8.26 |

We claim:

1. In a process of chlorinating butadiene to produce principally dichlorobutenes by feeding a reactor with a mixture of butadiene vapor and chlorine vapor, the butadiene to chlorine ratio being in excess of one mole of butadiene to one mole of chlorine, recovering the dichlorobutenes from the reactor and recycling unreacted butadiene back to the reactor;

the improvement which consists essentially of feeding the reactor with a mixture of butadiene vapor and chlorine vapor in a mole ratio of from 5:1 to 50:1 butadiene to chlorine, the entering vapor mixture being maintained at a temperature of from 70° to 175° C., maintaining the temperature of the vapor mixture in the reactor at from 70° to 250° C. whereby substantially all of the chlorine is reacted, conducting the product from the reactor to the lowest tray in a multiple tray scrubber-cooler and feeding makeup liquid butadiene to one or more upper trays of the scrubber-cooler, condensing the dichlorobutenes and separating them from unreacted butadiene while vaporizing the makeup liquid butadiene, the head temperature of the scrubber-cooler being maintained at from 45° to 80° C. by the makeup liquid butadiene and by recycling part of the scrubber-cooler bottom stream through a cooler and back to one or more upper trays of the scrubber-cooler, recycling the unreacted butadiene and the vaporized makeup butadiene from the scrubber-cooler to the reactor and recovering condensed dichlorobutenes.

2. The process of claim 1 wherein the mole ratio of butadiene to chlorine fed to the reactor is from 8:1 to 30:1.

3. The process of claim 2 wherein the gases in the reaction zone are maintained below 230° C.

4. The process of claim 3 wherein the head temperature of the scrubber-cooler is maintained at from 45° to 65° C.